United States Patent [19]

Fritzsch et al.

[11] Patent Number: 5,456,683
[45] Date of Patent: Oct. 10, 1995

[54] DISMANTALABLE MEDICAL INSTRUMENT

[75] Inventors: Gernod Fritzsch; Michael Hermle, both of Tuttlingen, Germany

[73] Assignee: Delma Elektro–Und Medizinisch Apparatebau Gesellschaft mbH, Tuttlingen, Germany

[21] Appl. No.: 274,178

[22] Filed: Jul. 12, 1994

[30] Foreign Application Priority Data

Jul. 14, 1993 [DE] Germany .......................... 43 23 584.0

[51] Int. Cl.[6] .................................................. A61B 17/36
[52] U.S. Cl. ................................. 606/41; 606/46; 606/50
[58] Field of Search .................................. 606/32, 37–51

[56] References Cited

U.S. PATENT DOCUMENTS

| | | | |
|---|---|---|---|
| 3,597,582 | 8/1971 | Goode | 606/45 |
| 4,016,881 | 4/1977 | Rioux et al. | 606/42 X |
| 4,493,319 | 1/1985 | Polk et al. | |
| 4,936,842 | 6/1990 | D'Amelio et al. | 606/42 |
| 5,275,612 | 1/1994 | Bales, Jr. | 606/205 |
| 5,300,069 | 4/1994 | Hunsberger et al. | 606/46 X |
| 5,322,503 | 6/1994 | Desai | 606/41 X |

FOREIGN PATENT DOCUMENTS

0589555A1 of 0000 European Pat. Off. .

*Primary Examiner*—Peter A. Aschenbrenner
*Attorney, Agent, or Firm*—Townsend and Townsend and Crew

[57] ABSTRACT

A dismantlable medical instrument has a central working rod (11) with working tools (25), a guide tube (12) and an outer tube (13). The working rod (11), the guide tube (12) and the outer tube (13) are releasably attached to a handle (14).

13 Claims, 1 Drawing Sheet

5,456,683

DISMANTALABLE MEDICAL INSTRUMENT

BACKGROUND OF INVENTION

The invention relates to a dismantlable medical instrument, in particular to a radio-frequency surgical instrument.

For medical instruments, particularly radio-frequency surgical instruments for the laparoscopic or minimally-invasive surgery, the problem of cleaning increasingly exists due to the range of instruments progressively becoming more complex. Instruments which are dismantlable to a greater or lesser degree are already known in order to solve this problem. A simultaneously optimum and complete cleaning is often problematic. For instruments with a displaceable working part, in particular with an axially displaceable working electrode, the assembly is often very difficult and not executable by unpracticed clinical personnel.

SUMMARY OF INVENTION

The invention is based on the object of providing a medical instrument, in particular a radio-frequency surgical instrument of the initially named kind, which can be cleaned in an optimum fashion and can also be dismantled and reassembled by unpracticed clinical personnel.

In order to satisfy this object, a dismantlable medical instrument is provided, in particular a radio-frequency surgical instrument comprising a central working rod, in particular an electrode tube at whose front end there are provided one or more working tools, in particular working electrodes, and at whose rear end there are provided, if necessary, connections for the supply of the working tools, in particular one or several radio-frequency voltage connections, a guide tube surrounding the working rod and preferably coaxial to it, optionally an outer tube surrounding the guide tube and preferably coaxial with it and a handle receiving the rear end of the working rod, the guide tube and optionally the outer tube, wherein preferably the guide tube is axially displaceable within a certain distance relative to the working rod for the operation of the working tools, characterized in that the handle, the working rod, the guide tube and optionally the outer tube are arranged to be separable from one another.

The inventive concept is to be seen in the fact that all parts which are preferably coaxially arranged relative to one another, in particular the working rod, the guide tube, optionally the outer tube and the tubularly formed handle, are arranged to be axially separable from one another, with the releasable connection during operation to be ensured by simple latched and/or lock and/or snap connections.

In one particularly advantageous embodiment, the same axial displacement mechanism is exploited for the relative displacement provided in operation between the working rod and the guide tube, and for the optionally desired separation between the guide tube and the guide sleeve. The axial displacement of the guide tube can for example serve the purpose of selectively pushing together or spreading apart two coagulating electrodes at the distal end of the instrument allowing it to grasp human tissue during the coagulation.

BRIEF DESCRIPTION OF THE DRAWINGS

The invention will now be described in the following by way of example and with reference to the drawing in which are shown.

DESCRIPTION OF THE PREFERRED EMBODIMENT

Figures 1, 2:
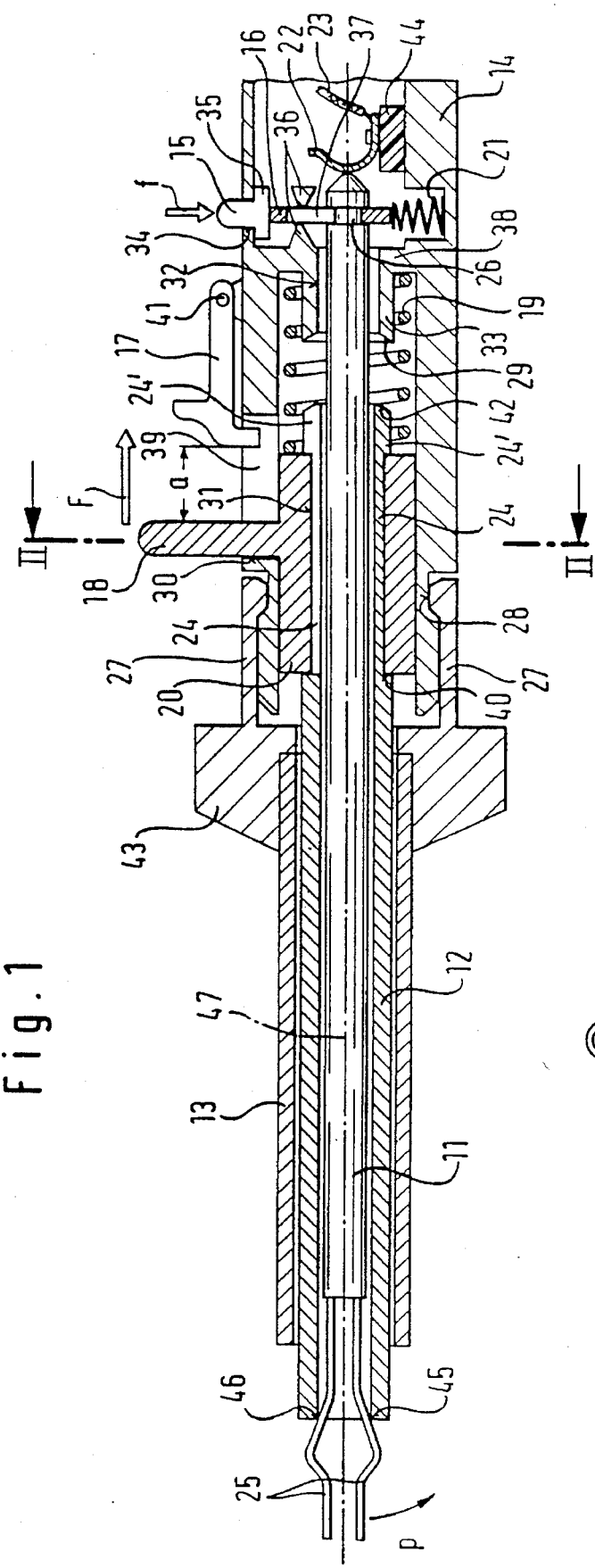
FIG. 1 is a partly sectioned side view of a radio-frequency surgical instrument in accordance with the invention.
FIG. 2 is a sectional view taken along the line II—II in FIG. 1.

In accordance with the drawings, an electrode tube 11 forming a central working rod and having two working electrodes 25 which are resiliently biased apart at its distal end extends coaxially to and through a guide tube 12. At its rear end the guide tube 12 carries latch tongues 24 which are uniformly distributed about the perimeter and which extend axially. The latch tongues 24 extend axially through a central bore 31 in a guide sleeve 20, which is arranged axially displaceable in a tubular actuation handle 14. The electrode tube 11 extends through the guide sleeve 20, and indeed radially within the latch tongues 24 in such a way as to prevent the disengagement of the latch tongues 24 and the guide sleeve 20. The rear end region of the electrode tube 11 extends through a bore 32 in a cam track 33 provided at a ring wall 38 fixed relative to the handle up to a coupling lock member 16 which is transversely displaceably mounted in the handle 14, and which is diametrically biased towards a push-button 15 by a latch spring 21. The push-button extends radially outward through a bore 34 in the wall of the handle 14, and the radially outward movement of the push-button is limited by a radially broadened portion 35 within the handle 14.

The coupling lock member 16 is guided in the direction transverse to the axis 47 of the instrument by transverse guides 36, which are merely schematically indicated, in such a way that it can bear axial loads. The coupling lock member 16 has a central opening 37 which surrounds the rear end region of the electrode tube 11 and the lower edge of the opening engages, via the latch spring 21, into a ring groove 26 provided in the electrode tube 11. Since the plate-like coupling lock member 16 and the ring groove 26 are complementary to one another, an axially form-locked engagement exists between the coupling lock member 16 and the electrode tube 11. This prevents an axial displacement of the electrode tube 11 within the handle 14 and preferably in addition prevents the otherwise possible rotation of the electrode tube 11 about the axis 47. The biasing force of latch spring 21 provides sufficient friction between the lower edge of opening 37 and ring groove 26 to inhibit rotation of electrode tube 11 about axis 47.

By pressing the push-button 15 in the direction of the arrow f, the interlocking connection between the coupling lock member 16 and the rear end region of the electrode tube 11 can be released, whereby the electrode tube 11 can be forwardly withdrawn from the guide tube 12.

The guide sleeve 20 is forwardly biased by a resetting spring 19 which is braced against a ring wall 38. An actuation trigger 18 which projects radially from the guide sleeve 20 through an axially elongated radial slot 39 of the handle 14 is pressed via the resetting spring 19 against an abutment 30 formed by the front end of the radial slot 39, whereby the forward displacement of the guide tube 12 is limited.

The latch tongues 24 merge into the guide tube 12 at the forward end via a ring step 40, whereby a rearward displacement of the guide tube 12 relative to the guide sleeve 20 is prevented. The latch heads 24' of the latch tongues 24 engage behind the rear end of the guide sleeve 20 in such a way that in the latched condition, a forward movement of the guide tube 12 relative to the guide sleeve 20 is prevented as well.

A catch hook 17 which is upwardly pivotable about a transverse hinge 41 engages into the radial slot 39 from the rear, and indeed only so far that there is still a distance a between the front end of the catch hook 17 and the rear end of the actuation trigger 18. The guide tube 12 can be displaced within the distance a through corresponding displacement of the actuation trigger 18 in the direction of the arrow F against the bias of the resetting spring 19.

The arrangement of the catch hook 17 is such that even in the case that the actuation trigger 18 completely traverses the distance a, the rear end 42 of the latch tongues 24 does not quite contact the front end 29 of the cam track 33; however, it is very close to it.

An outer tube 13 which is likewise of right cylindrical shape is slid coaxially over the guide tube 12, with the outer tube having at its rear end region a ring-shaped attachment member 43, which at its rear end has axially projecting latch arms 27, which axially overlap the front end of the tubular handle 14 and which externally releasably engage with a ring-shaped latch groove 28 provided immediately in front of the abutment 30.

The rear ends 42 of the latch heads 24' are conically formed in accordance with the invention, while the front end face of the cam track 33 is formed complementary to the ends 42 as a cam track 29.

At the end of the electrode tube 11 there is an electrically conductive contact spring 22 which is attached to an insulating block 44 and which is connected in an electrically conductive manner to a high-voltage lead 23.

When—as shown in FIG. 1—two mutually insulated working electrodes 25 are provided, two separated contact springs 22 must correspondingly be arranged next to one another at the rear end of the electrode tube 11 and connected to two radio-frequency voltage leads.

The manner in which the described radio-frequency surgical instrument operates is as follows:

During normal operation a radio-frequency voltage is applied to the two electrodes 25. By displacing the trigger 18 in the direction of the arrow F within the distance a, the guide tube 12 can be displaced to the rear relative to the electrode tube 11, whereby the front diametrically opposing inner edges 45, 46 of the guide tube 12 slide rearwardly on the radially outward flanks of the two working electrodes 25, which causes the lower electrode 25 and the upper electrode to spread resiliently apart from one another in the direction of the arrow p and in the opposite direction. On subsequently pushing the guide sleeve 20 forward, which occurs through the force of the spring 19 when the displacing force disposed towards the direction of arrow F disappears, the edges 45, 46 slide forward on the electrodes 25 and resiliently move them towards one another.

Thus, by displacing the trigger 18 rear and forth, a movement in the manner of forceps of the two working electrodes 25 relative to one another can be obtained.

If the instrument is to be dismantled, then this can occur by first pushing the push-button 15 in the direction of the arrow f, whereby the coupling lock member 16 disengages from the electrode tube 11. The electrode tube 11 can then be completely withdrawn from the guide tube 12 in a forward direction.

Then the catch hook 17 is pivoted upwardly about its hinge 41, whereby in addition the rear region of the radial slot 39 becomes accessible to the trigger 18. The trigger can thus be further displaced towards the rear by a distance beyond the normal operating distance a, with the rear end 42 of the latch heads 24' engaging with the cam track 29.

Because of the inclination of the surfaces 42, 29 which engage with one another as shown in the drawing and because of the fact that the electrode tube 11 is already withdrawn, the latch tongues 24 now deflect radially inward and thus axially disengage from the guide sleeve 20. Now a small axial clearance must be available within the radial slot 39, so that the guide sleeve 20 slides over the outer perimeter of the latch heads 24' after the disengagement of the latch heads 24' from the guide sleeve 20.

At this point, the axial engagement between the latch tongues 24 and the guide sleeve 20 which keeps the guide tube 12 from being forwardly withdrawn is removed, so that now the guide tube 12 can be forwardly withdrawn from the outer tube 13.

Afterwards, the latch arms 27 of the attachment member 43 must be removed from the ring-shaped latch groove 28, which can be brought about either by a tool or by a sufficiently large axial withdrawal force, as long as the forward flanks of the latch groove 28—as shown in FIG. 1—are formed in a somewhat inclined manner.

The instrument is now completely dismantled, and the four individual parts obtained, in particular the electrode tube 11, the guide tube 12, the outer tube 13 as well as the handle 14 can now be subjected to an intensive cleaning and optionally a serialization.

We claim:

1. A radio-frequency surgical instrument capable of being dismantled comprising:

a central working rod having proximal and distal ends and a longitudinal axis therebetween, the distal end forming at least one electrode and the proximal end being adapted for connection to a source of radio-frequency voltage;

a guide tube surrounding the working rod and having distal and proximal ends, the guide tube being axially movable relative to the working rod to actuate the electrode;

a handle coupled to the proximal ends of the working rod and the guide tube, the working rod being releasably attached to the handle at a release point near the proximal end of the working rod; and a guide sleeve disposed within the handle and surrounding a portion of the guide tube, the guide sleeve coupling the guide tube to the handle distal of the release point, the guide sleeve including external means for releasing the guide tube from the handle.

2. The instrument of claim 1 wherein the guide tube further includes a plurality of latch tongues extending from the proximal end of the guide tube, the latch tongues engaging a proximal end of the guide sleeve to prevent distal movement of the guide tube relative to the handle and the guide sleeve, the handle further including a cam track positioned proximally from the guide sleeve such that, when the guide sleeve is axially displaced in the proximal direction a predetermined distance relative to the handle, the cam track engages the latch tongues and displaces the latch tongues radially inwardly such that the latch tongues disengage from the guide sleeve.

3. The instrument of claim 1 wherein the handle includes an abutment and a spring, the spring biasing the guide tube in the distal direction against the abutment.

4. The instrument of claim 2 wherein the handle further includes an axial slot for receiving a portion of the guide sleeve such that the guide sleeve and the guide tube together are axially movable over a first displacement range with respect to the handle, the handle further including a releasable catch mounted to an outside surface of the handle and movable between a first position, where the guide sleeve and the guide tube are prevented from moving further than the first displacement range, and a second position, where the guide sleeve and guide tube are axially movable over a second displacement range, the second displacement range being further than the first displacement range.

5. The instrument of claim 4 wherein the latch tongues engage the cam track when the releasable catch is in the second position so that the latch tongues disengage from the guide sleeve thereby allowing the guide tube to be separated from the guide sleeve and the handle.

6. The instrument of claim 1 further comprising an outer tube surrounding the guide tube and releasably fixed to the handle.

7. A medical instrument capable of being dismantled comprising:
- a central working rod having proximal and distal ends and a longitudinal axis therebetween, the distal end forming at least one working tool;
- a guide tube surrounding the working rod and having distal and proximal ends, the guide tube being axially movable relative to the working rod;
- a handle coupled to the proximal ends of the electrode tube and the guide tube, the working rod being releasably attached to the handle at a release point near the proximal end of the working rod; and
- a guide sleeve disposed within the handle and surrounding a portion of the guide tube, the guide sleeve coupling the guide tube to the handle distal of the release point, the guide sleeve including external means for releasing the guide tube from the handle.

8. The instrument of claim 7 wherein the guide tube further includes a plurality of latch tongues extending from the proximal end of the guide tube, the latch tongues engaging a proximal end of the guide sleeve to prevent distal movement of the guide tube relative to the handle and the guide sleeve, the handle further including a cam track positioned proximally from the guide sleeve such that, when the guide sleeve is axially displaced in the proximal direction a predetermined distance relative to the handle, the cam track engages the latch tongues and displaces the latch tongues radially inwardly such that the latch tongues disengage from the guide sleeve.

9. The instrument of claim 7 wherein the handle includes an abutment and a spring, the spring biasing the guide tube in the distal direction against the abutment.

10. The instrument of claim 8 wherein the handle further includes an axial slot for receiving a portion of the guide sleeve such that the guide sleeve and the guide tube together are axially movable over a first displacement range with respect to the handle, the handle further including a releasable catch mounted to an outside surface of the handle and movable between a first position, where the guide sleeve and the guide tube are prevented from moving further than the first displacement range, and a second position, where the guide sleeve and guide tube are axially movable over a second displacement range, the second displacement range being further than the first displacement range.

11. The instrument of claim 10 wherein the latch tongues engage the cam track when the releasable catch is in the second position so that the latch tongues disengage from the guide sleeve thereby allowing the guide tube to be separated from the guide sleeve and the handle.

12. The instrument of claim 7 further comprising an outer tube surrounding the guide tube and releasably fixed to the handle.

13. A radio-frequency surgical instrument capable of being dismantled comprising:
- a central working rod having proximal and distal ends and a longitudinal axis therebetween, the distal end forming a pair of electrode jaws and the proximal end being adapted for connection to a source of radio-frequency voltage;
- a guide tube surrounding the working rod and having distal and proximal ends, the guide tube being axially movable relative to the working rod to open and close the electrode jaws;
- a handle coupled to the proximal ends of the working rod and the guide tube, the handle including an actuator for releasing the working rod; and
- a guide sleeve disposed within the handle and surrounding a portion of the guide tube, the guide sleeve being releasably attached to the guide tube and having a trigger member projecting out of the handle, the trigger member being movable between first and second positions so to move the guide tube relative to the working rod and thereby open and close the electrode jaws, the trigger being further movable into a third position to disengage the guide tube from the guide sleeve and the handle.

* * * * *

UNITED STATES PATENT AND TRADEMARK OFFICE
CERTIFICATE OF CORRECTION

PATENT NO. : 5,456,683

DATED : October 10, 1995

INVENTOR(S) : GERNOD FRITZSCH et al.

It is certified that error appears in the above-identified patent and that said Letters Patent is hereby corrected as shown below:

On the title page, item [73], the Assignee should read:

Delma elektro- und medizinische Apparatebau Gesellschaft mbH,
Tuttlingen, Germany Signed and Sealed this Fourteenth Day of May, 1996

*Attest:*

BRUCE LEHMAN

*Attesting Officer*        *Commissioner of Patents and Trademarks*